United States Patent [19]

Graham, Jr. et al.

[11] 4,296,090

[45] Oct. 20, 1981

[54] ANTI-D TEST AND REAGENT

[75] Inventors: Henry A. Graham, Jr.; David J. Olekna, both of Annandale; Johnna B. Hawk, Rocky Hill; Diane M. Barrett, Somerville, all of N.J.

[73] Assignee: Ortho Diagnostics, Inc., Raritan, N.J.

[21] Appl. No.: 82,199

[22] Filed: Oct. 5, 1979

Related U.S. Application Data

[63] Continuation-in-part of Ser. No. 57,481, Jul. 13, 1979, abandoned.

[51] Int. Cl.$^3$ ............................................. G01N 33/80
[52] U.S. Cl. ................................... 424/11; 23/230 B; 252/408; 260/112.5 R; 424/12
[58] Field of Search ...................... 23/230 B; 252/408; 424/11; 260/112.5

[56] References Cited

U.S. PATENT DOCUMENTS

| | | | |
|---|---|---|---|
| 2,454,752 | 11/1948 | Coca | 424/11 |
| 2,761,810 | 9/1956 | Singher | 424/11 |
| 2,761,811 | 9/1956 | Kupferberg | 424/11 |
| 3,579,627 | 5/1971 | Hayakawa | 424/11 |
| 3,880,988 | 4/1975 | Fly | 424/11 |

OTHER PUBLICATIONS

"A Seminar on Performance Evaluation", Byron A. Myhre, ed., presented at the 29th Annual Meeting of the American Association of Blood Banks in San Francisco, Calif. on Nov. 2, 1976, American Association of Blood Banks, Central Office, Suite 608, 1828 L Street, N.W., Washington, D.C. 20036.

Romans, et al. Proc. Natl. Acad. Sci., U.S.A., 74(6), 2531–2535 (1977).

Laschinger, et al., Abstract (report of the Combined Meeting of the XVII Congress of The International Society of Hematology and The XV Congress of the International Society of Blood Transfusion, Jul. 24–28, 1978).

Primary Examiner—Sidney Marantz
Attorney, Agent, or Firm—Geoffrey G. Dellenbaugh

[57] ABSTRACT

Methods and reagents for determination of Rh (D) antigen in human blood. The reagent is a low-protein composition containing reduced and S-alkylated anti-D IgG maintained at pH of between about 7.5 and 8.3. This reagent meets or exceeds FDA standards for potency of anti-D for the slide test of rapid tube test.

14 Claims, 6 Drawing Figures

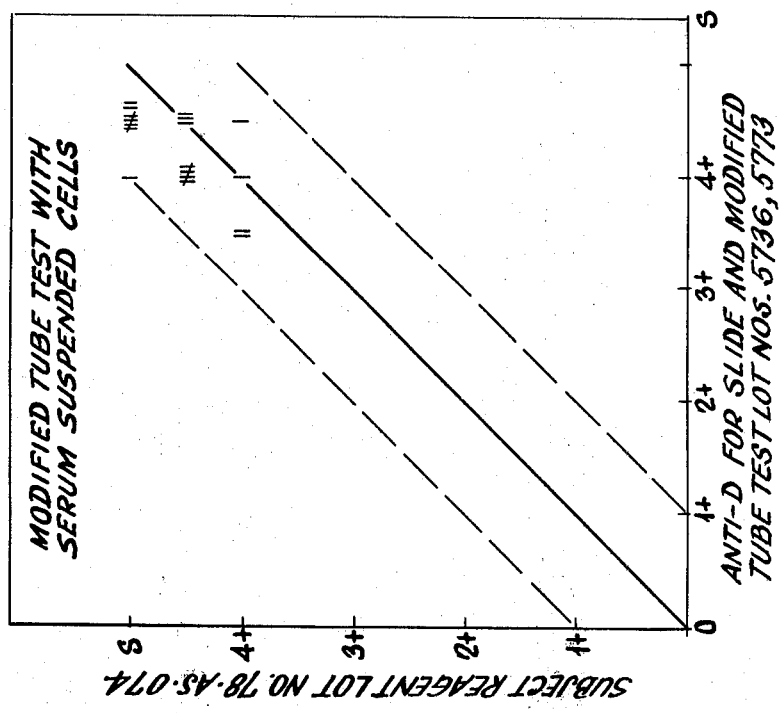
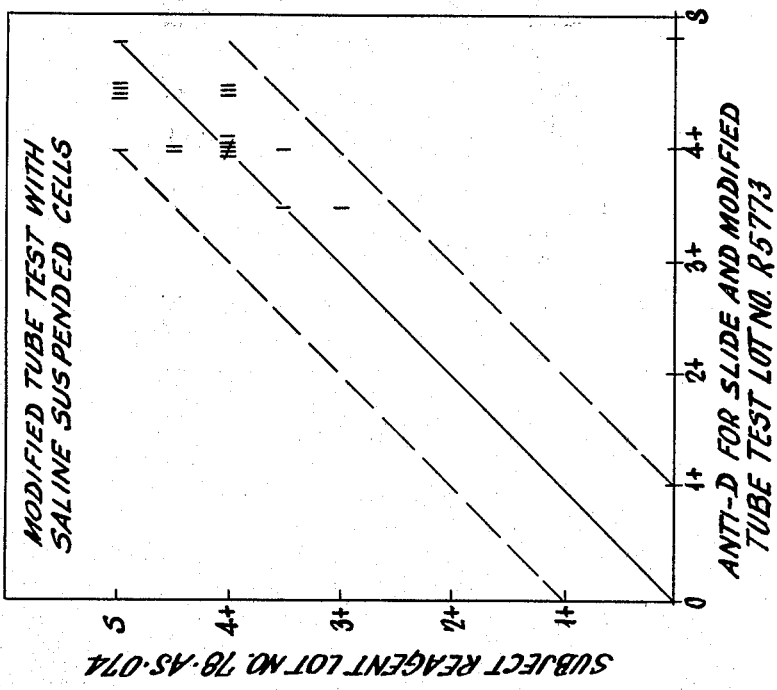

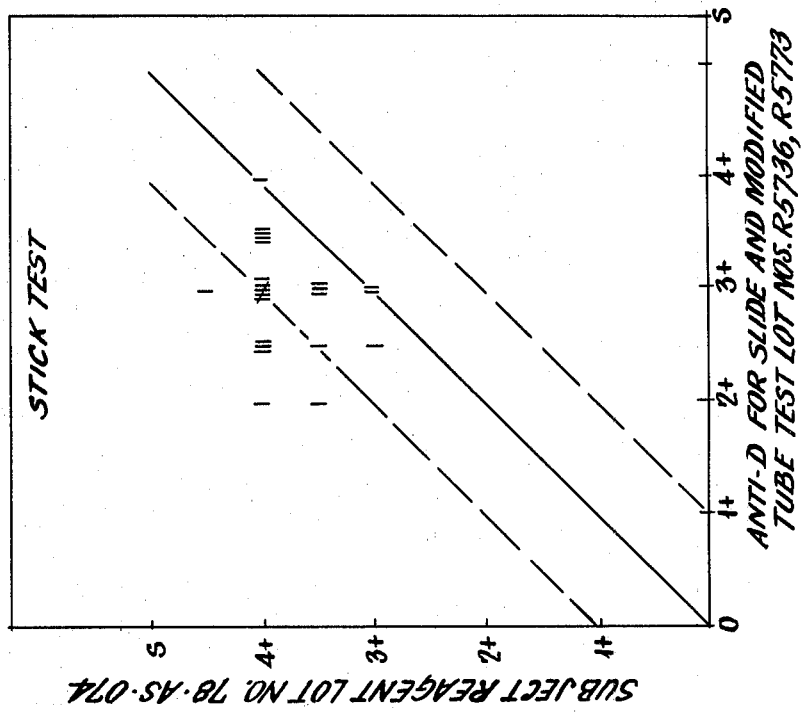
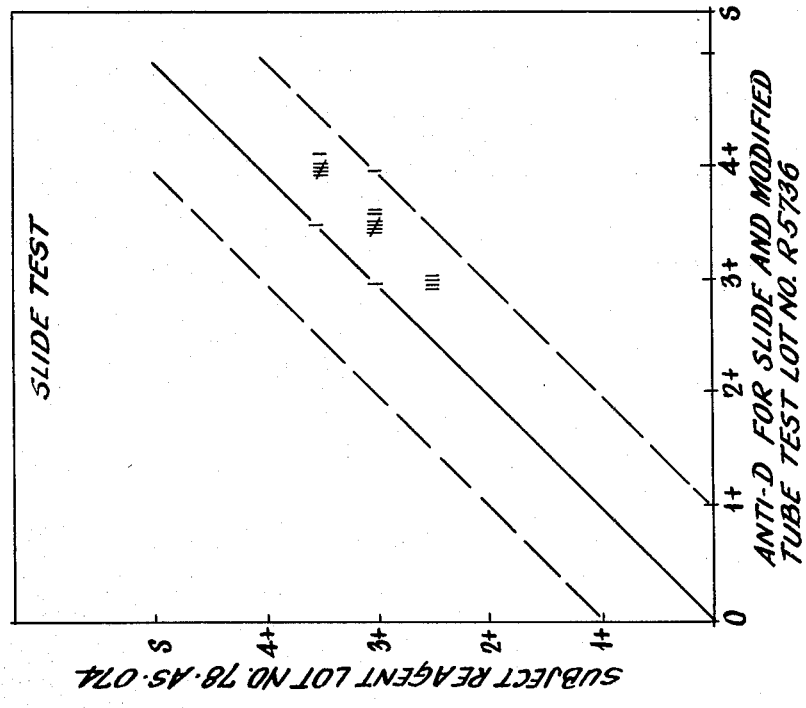

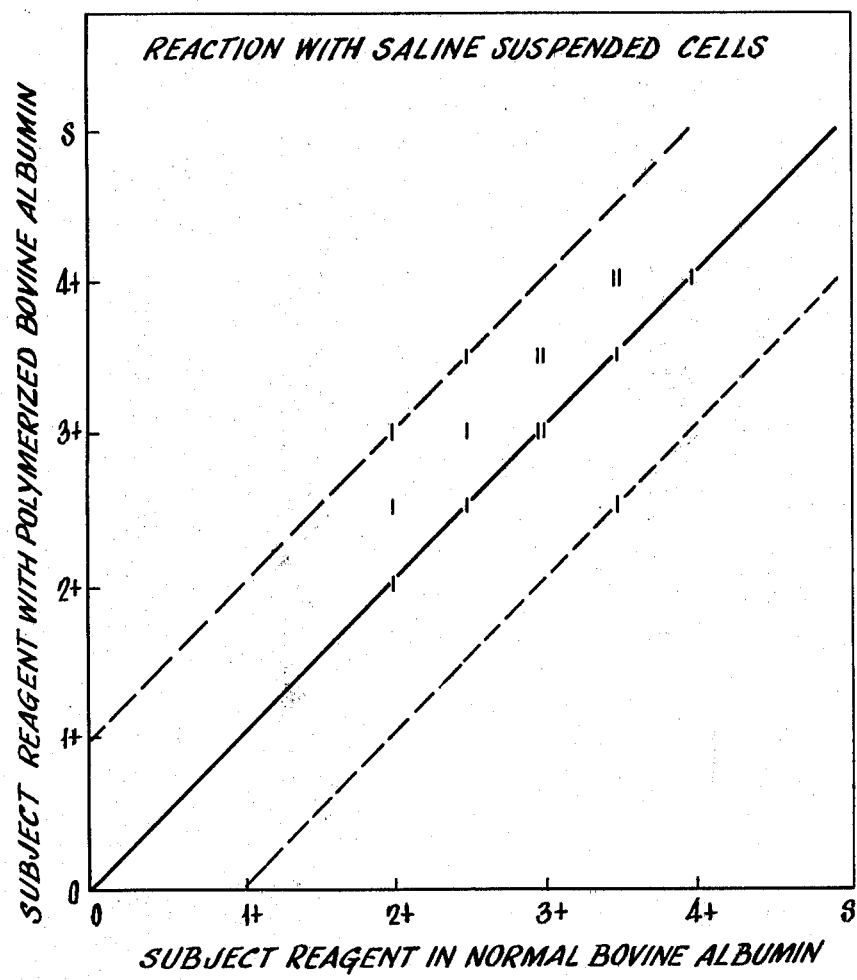

ANTI-D TEST AND REAGENT

REFERENCE TO RELATED APPLICATION

This application is a continuation-in-part application of our copending application Ser. No. 57,481, filed July 13, 1979, now abandoned.

TECHNICAL FIELD

The present invention relates to methods and reagents for use in blood typing and more specifically for the detection of Rh (D) antigen.

BACKGROUND OF THE INVENTION

Blood typing, and particularly the determination of the presence or absence of Rh (D) antigen, is a routine procedure in modern medicine. Since the discovery of the relationship between Rh factor and disease in the 1930's, there has been an increasing concern to detect Rh incompatibilities between mother and fetus so that such incompatibilities may be treated or avoided in future children. At the present time, many state laws require Rh testing of pregnant women and of infants born of Rh negative women. The introduction of Rh immune globulin in 1968 allowed for the first time a method of treatment of Rh negative women bearing Rh positive children to prevent disease in later Rh positive children of these women.

The United States Food and Drug Administration (FDA) requires that an anti-D antiserum have a potency titer value at least equal to that of the FDA reference serum, as set out in a chapter entitled "Performance Criteria For Blood Grouping Sera" authored by P. A. H. Hoppe from the Immunohematology Branch, Division of Blood and Blood Products, Bureau of Biologics, Food and Drug Administration. Appendix I of this publication presents observed titer values of the anti-D (slide and rapid tube) FDA reference serum, which vary from twenty-nine to fifty-eight, depending upon the test call phenotype used. In other words, the reference serum gave a reaction rated as "one plus" at dilutions varying from 1:32 to 1:64 (titers of 32 to 64). This appendix I demonstrates that an anti-D product meets the FDA potency requirements if it has an average titer of at least 32 for Dce cells in the slide tests or rapid tube test.

There are two types of diagnostic tests currently used for detecting the presence of D antigen. It should be understood, by way of introduction, that IgG antibody to D antigen is a so-called "incomplete" antibody. That is, IgG antibodies with specificity for the D antigen often fail to agglutinate Rh positive red cells suspended in saline. In contrast, IgM antibodies to the D antigen do cause agglutination of Rh positive red cells in saline.

The first of these tests uses IgG anti-D antibody as the reagent. Since anti-D IgG will not by itself cause agglutination of Rh positive red blood cells in saline, some potentiating means must be found to cause the agglutination. This potentiation is accomplished by a relatively high concentration of a biological polymer (e.g., nonspecific protein such as albumin) or a synthetic polymer (e.g., polyvinylpyrrolidone or a dextran). Typically, the concentration of albumin in the final reagent composition is approximately 20 to 25 percent. While this added protein succeeds in potentiating the agglutination of specific IgG anti-D antibodies and red blood cells having D antigen, it also causes nonspecific agglutination of red blood cells having IgG coated on the surface thereof. Such coating occurs, for example, in individuals having such diseases as autoimmune hemolytic anemia or hemolytic disease of the newborn, in which antibody is produced to the patient's own red blood cells and binds thereto. False positive results for presence of Rh antigen will therefore be obtained for these individuals with this test. One significant advantage of this test, however, is its rapidity, since little (if any) incubation is required prior to reading the results. This test may be conducted in either a test tube or a glass slide. A second advantage is the ability to detect certain weak antigens denominated $D^u$, as further described below.

The second current test for detection of D antigen uses IgM antibody instead of IgG antibody. Since IgM is a complete antibody with respect to the D antigen, the addition of a potentiator is not required; typically, the reagent composition contains a total protein concentration of less than about 8% by weight, accomplished by adding (e.g.) bovine albumin to the IgM antiserum. This test can be conducted only in a test tube. While this test removes the nonspecific agglutination of IgG coated cells which occurs with the potentiated IgG test, it also suffers from several disadvantages. The principal disadvantages are that the test requires a fifteen to sixty minute incubation at 37° C., which step is not required by the potentiated IgG test, and also that it requires IgM antibody, which is rare and difficult to obtain. Additionally, it is not possible to run the so-called $D^u$ test in conjunction with this second type of test, since this $D^u$ test uses antibody to IgG as its reagent. This reagent antibody obviously does not react with IgM.

Thus, if one could develop a rapid test employing IgG antibody in a low protein formulation, a long felt need would be satisfied.

PRIOR ART

The conversion of incomplete anti-D IgG to a direct saline agglutinin by reductive cleavage of the disulfide bonds has been described in several articles. It was first reported in 1960 by Chan and Deutsch (J. Immunol. 85:37–45) and then in 1963 by Pirofsky and Cordova (Nature, 197, 392–393), but these findings were called into question in 1965 by Mandy, et al., (J. Clin. Invest., 44, 1352–1363). Additional work confirming the conclusions of Pirofsky and Cordova was reported in 1977 by Romans, et al., [Proc. Natl. Acad. Sci. USA, 74 (6), 2531–2535]. In this article, however, agglutination was achieved only in a test tube after a two hour incubation of red blood cells and reduced anti-D IgG. Moreover, although this Romans, et al., article teaches that incomplete IgG antibodies may be converted to complete antibodies by reduction, there is no teaching of any specific procedure or reagent (let alone one meeting FDA standards) for use in conducting an Rh typing test. In fact, the article indicates in the last sentence that there may be some question as to whether the reduced antibody will be practical for use as a typing reagent, referring to certain unpublished studies then in progress.

In the report of the combined meeting of the XVII Congress of the International Society of Hematology and the XV Congress of the International Society of Blood Transfusion, July 24–28, 1978, there was published an abstract which appears to disclose some of the work referred to in the Romans, et al., paper. This Laschinger, et al., abstract reports "the production and testing of a reliable monospecific anti-D agglutinin with a titer of 16 from a pool of incomplete anti-D sera." This reported titer gives no assurance that the material produced met FDA standards. No information is given in the abstract relating to the method by which this agglutinin was produced, the test method used, or the amount of incubation necessary to achieve agglutination.

SUMMARY OF THE INVENTION

The present invention provides a rapid method for detecting $Rh_0$ (D) antigen and reagents for practicing this method which remove the disadvantages attendant on the prior art methods. The subject antibody reagent allows for the first time the use of IgG antibody in a low-protein slide or rapid tube test. The subject test has no nonspecific reaction with IgG coated cells due to the low-protein content. Moreover, the subject antibody reagent meets and exceeds FDA standards for potency of anti-D for the slide test or rapid tube test. These FDA standards are contained in Subpart C of Part 660, Subchapter F of the Federal Food, Drug and Cosmetic Act (see 42 Federal Regulations 54542 ff, No. 195, Oct. 7, 1977).

The anti-D reagent is generally prepared by the following procedure. Serum is obtained from individuals having high levels of anti-D IgG in their bloodstream and is treated to remove certain contaminants and purify the IgG. While the specific method of producing the anti-D antiserum for use in preparing the subject reagent is not part of the present invention, one suitable process is the following. Other processes for producing suitable anti-D antisera are known.

If necessary, the plasma is defibrinated with an appropriate amount of bovine thrombin; decalcified with sodium oxalate; clarified by centrifugation; and neutralized by the addition of blood group specific substance A and/or AB.

Lipids are substantially removed from the serum by extraction with trichlorotrifluoroethane. The serum is heated to a maximum of 56.6° C. and then cooled to 2°–8° C., after which trichlorotrifluoroethane is blended in at high speeds until the serum foams. After the serum has been stored at 2°–9° C. until the foam dissipates, it is centrifuged, heated again, and stored at 2°–8° C. The pH is adjusted to 7.3–8.3 and the serum is stored at −20° C. or below.

This substantially lipid-free serum may then be treated in the following manner to produce the subject reagent.

The pH of the substantially lipid-free serum is adjusted to about 8.6 using an effective amount of a compatible buffer such as 2 M tris-(hydroxymethyl)aminomethane (TRIS). One volume of 0.04 M dithiothreitol in saline is added to about four volumes of the buffered serum and the mixture is allowed to stand at about 20°–30° C. for a minimum of about thirty minutes.

Following this treatment, one volume of 0.4 M iodoacetamide in distilled water is added to about four volumes of the treated serum. This mixture is allowed to stand at about 20°–30° C. for a minimum of about sixty minutes. The resulting serum is then dialyzed twice at 2°–8° C. using ten volumes of freshly prepared 0.15 M TRIS buffer at pH 7.5–8.3 and preferably pH 7.7–8.1 each time. After the second dialysis, sodium azide is added to the treated serum to a final concentration of 0.1% as a preservative, and the total protein concentration is adjusted to about 6–10 weight percent with bovine albumin. Polymerized bovine serum albumin as disclosed in U.S. Pat. No. 4,140,662 is preferably used.

While one particular process for producing the subject reagent has been given above, it is contemplated that other suitable reducing agents may be substituted for the preferred dithiothreitol used therein; such reducing agents include, for example, 2-mercaptoethanol and dithioerythritol. While iodoacetamide is used above as the S-alkylating agent, it is clearly contemplated that other alkylating agents may be used, for example, iodoacetic acid. Alternately, equivalent methods of preventing reformation of the disulfide bond may be used.

The pH range of 7.5–8.3 and preferably 7.7–8.1 is important to the proper functioning of the subject reagent. Outside the 7.5–8.3 pH range, the reactions of the subject antibody reagent tend to be somewhat weaker. While this pH range may be maintained by an effective buffering amount of any compatible buffer (i.e., one which has no adverse effect on the anti-D antibodies or the red blood cells), TRIS buffer is preferred.

The present invention provides improved methods for rapidly determining the presence or absence of the D antigen on red blood cells of a given individual using the reagent described above. It is anticipated that any of the prior art rapid typing methods, such as the slide test, modified ("rapid") tube test, or stick test method, may be employed, but substituting the subject reagent for the prior art IgG antiserum used therein. While directions for the use of the subject antibody reagent in certain prior art tests are given below, it is anticipated that the use of the subject antibody reagent is not limited to those specific tests but may be used generally in any method which comprises the steps of:

(A) Obtaining a sample of red blood cells to be tested;
(B) Adding to and mixing with said sample the subject antibody reagent to form a mixture; and
(C) Without incubation observing said mixture to determine whether agglutination does or does not occur.

The term "without incubation" as used herein is intended to mean that no deliberate delay occurs prior to the observing step. This is in contrast to the description the Romans, et al., article where a substantial incubation step occurs.

The modified tube method may be conducted as follows. First, a suspension of the red blood cells to be tested is prepared. Conveniently, this may be a five percent suspension in normal group compatible serum, in the patient's own serum or plasma, or in isotonic saline.

Second, a small amount (conveniently one drop) of the subject antibody reagent is mixed with an equal amount of the red blood cell suspension in a small test tube, after which the tube is centrifuged without prior incubation to produce a "button" of red cells and a clear supernate, as known in the art.

Finally, the presence or absence of agglutination is determined, for example by resuspending the cells by gentle agitation and macroscopically examining them. If desired, a control of saline or nonspecific protein (e.g., 6–8% bovine albumin) in saline may be employed to aid in this determination.

A slide test may be performed as follows. First, a suspension of the red blood cells to be tested is again prepared in normal group compatible serum or in the patient's own serum or plasma. Whole blood may be used without dilution, since the concentration of red blood cells in the test sample conveniently should be about 40–50%.

Second, a small amount (e.g., about one drop) of the subject antibody reagent is mixed with about double the volume of the cell suspension on a prewarmed glass slide. Preferably, the temperature of the slide is about 40°–45° C., although ambient temperatures (e.g., 20°–30° C.) may be used.

Finally, after the red blood cell suspension and the antibody reagent have been thoroughly mixed but without further incubation, the presence or absence of agglutination is evaluated by tilting the slide back and forth for several minutes and observing for any agglutination. A control of saline or nonspecific protein (e.g., 6–8% bovine albumin) in saline may also be subjected to the same series of steps in place of the subject antibody reagent for use as a negative control.

Negative results on any of these tests may be confirmed by the $D^u$ test as follows. To a small amount of the five percent suspension of red blood cells referred to above is added an equivalent amount of the subject antibody reagent with mixing. After incubation of this mixture at about 37° C. for about 15 minutes, the cells are washed, preferably three times with isotonic saline, and antihuman serum is added to the washed cells. The cells are then centrifuged as described above and the presence or absence of agglutination is determined by observation. A positive result on this test (but negative on the D test and control) indicates Rh positive cells of the $D^u$ variety. A saline suspension of the same red blood cells (without antibody reagent) is used as a control.

While these methods of use of the subject antibody reagent have been given by way of illustration, it is anticipated that the subject reagent is suitable for use in any agglutination test for detection of Rh antigen and especially for use in such tests which do not require incubation.

The present invention will be further described with reference to the following Figures.

DETAILED DESCRIPTION OF THE DRAWINGS

FIG. 2 is a comparison of a lot of the subject reagent with commercial anti-D serum for slide and modified tube test, in which both reagents are used to perform a modified tube test;

FIG. 3 shows the same comparison as FIG. 2 in which the reagents are reacted with serum suspended test cells;

FIG. 4 illustrates the same comparison as FIGS. 2 and 3, but for the stick test;

FIG. 5 illustrates the same comparison for a slide test; and

FIG. 6 illustrates a comparison of the subject reagent with polymerized bovine albumin and normal bovine albumin.

Figure 1:
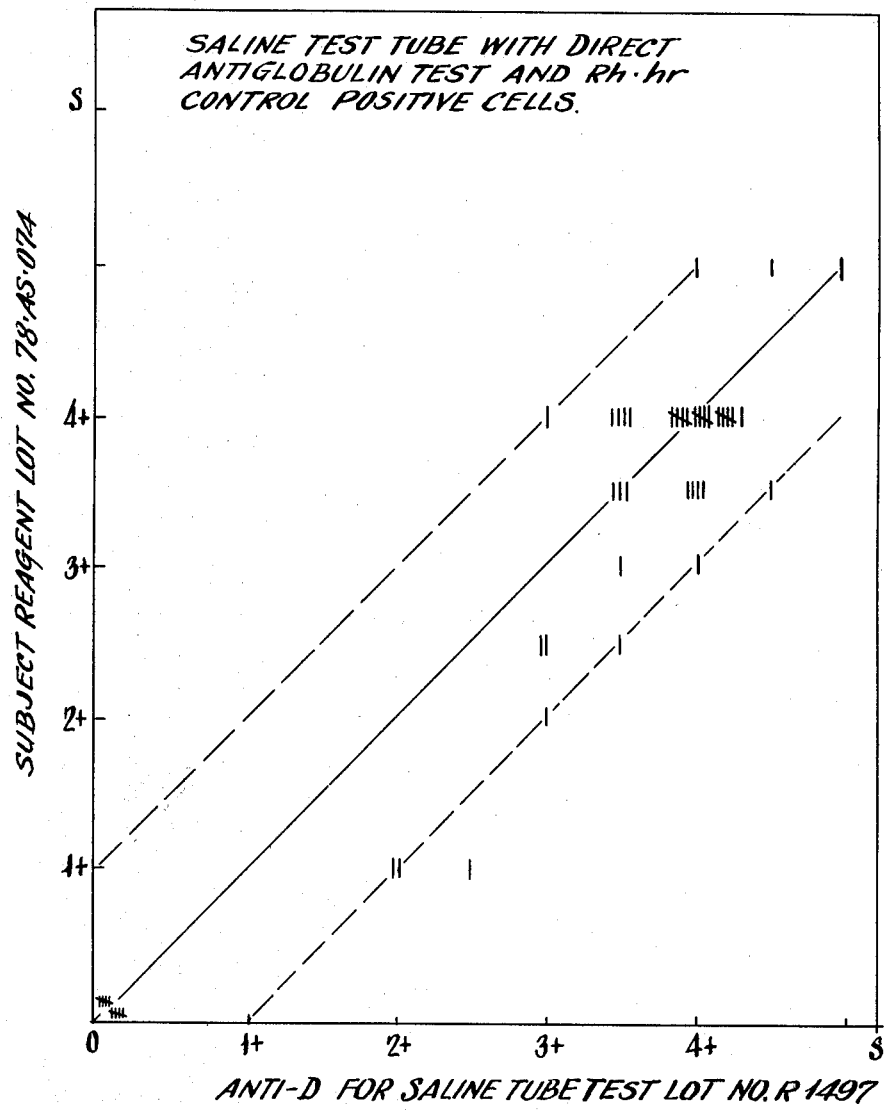
FIG. 1 is a comparison of a lot of the subject reagent with commercial anti-D serum for saline tube test.

The performance of the subject antibody reagent has been demonstrated in tests which compared it to current anti-D reagents for slide and modified tube tests and for saline tube test, respectively. As a result of these tests, the subject antibody reagent performs at least as well as current anti-D reagents, and, because of its unique characteristics, offers significant advantages.

The specificity of the subject antibody reagent Lot 78-AS-074 was demonstrated in comparison with Ortho anti-D serum for saline tube test Lot R1497. For this test, 284 direct antiglobulin test positive red blood cells (as determined with polyspecific anti-human serum) were selected. These direct antiglobulin test positive cells were selected because they are likely to spontaneously agglutinate in a high protein medium such as that used in prior art IgG antibody reagents. Hence they provide a good panel of cells for demonstration of the advantages of the subject antibody reagent, which has a relatively low protein concentration. Of these cells, 55 reacted with Ortho Rh-hr Control (reagent solution without antibody), which would invalidate test results obtained with a high protein, high viscosity reagent such as anti-D serum for slide and modified tube test. Hence, these 55 cells could be successfully tested using the subject antibody reagent but not the prior art high protein IgG antibody reagent. Three of the 55 cells agglutinated with saline and could not be tested by routine procedures. The remaining 52 cells were tested according to the saline tube test procedures recommended in the labelling. The results are graphically depicted in FIG. 1. Ten cells exhibited negative reactions with both reagents. Forty-two cells exhibited positive reactions, of comparable strength, with both reagents. From these results, it can be concluded that the subject antibody reagent is as specific as Ortho anti-D serum for saline tube test, and that it can be used in tests where Ortho anti-D serum for slide and modified tube test gives nonspecific reactions.

The subject antibody reagent Lot 78-AS-074 was compared with Ortho anti-D serum for slide and modified tube test, Lots R5736 and R5773, by performing modified tube tests, stick tests, and slide tests according to the procedures recommended in the labelling. The modified tube tests were performed using saline suspended test cells and serum suspended test cells, respectively. The results obtained with the saline suspended test cells appear in FIG. 2, and indicate that the reactions with the two antisera are comparable. The results obtained with the serum suspended test cells appear in FIG. 3. From these results, the reactions with the subject antibody reagent appear to be slightly stronger than the reactions with anti-D serum for slide and modified tube test. The stick test reactions depicted in FIG. 4 indicate that reactions with the subject antibody reagent are stronger. The results of the slide test appear in FIG. 5. In these tests the subject antibody reagent exhibited slightly weaker reactions than anti-D serum for slide and modified tube test. The use of polymerized bovine serum albumin (FIG. 6) improves the strength of the agglutination. The figure shows the strength of agglutination for each composition with 2 to 3 week old red cells (3–5%) suspended in saline.

In FIGS. 1–6, the degree of agglutination is represented by the designations 0, 1+, 2+, 3+, 4+, and S, in which 0 designates no observable agglutination, 1+ through 4+ designate progressively greater degrees of agglutination, and S designates "solid" or maximum agglutination.

The scope of the invention is defined in the following claims.

What is claimed is:

1. A method for rapidly determining the presence or absence of D antigen on the red blood cells of a given individual which comprises the steps of:
    (a) obtaining a sample of red blood cells to be tested;
    (b) adding to and mixing with said sample an antibody reagent to form a mixture; and (c) without incubation observing said mixture to determine whether agglutination does or does not occur;

wherein said antibody reagent comprises reduced and S-alkylated anti-D IgG which has an average titer of at least 32 for Dce cells in the slide test or rapid tube test.

2. The method of claim 1 wherein the antibody reagent is maintained at a pH of between about 7.5 and 8.3.

3. The method of claim 2 wherein the antibody reagent further comprises a total protein concentration of from about 6–10% by weight.

4. A slide test method for rapidly determining the presence or absence of D antigen on the red blood cells of a given individual which comprises the steps of:
   (a) obtaining a sample of red blood cells to be tested;
   (b) adding to and mixing with said sample on a test slide, an antibody reagent to form a mixture; and
   (c) without incubation observing said mixture to determine whether agglutination does or does not occur;

wherein said antibody reagent comprises reduced and S-alkylated anti-D IgG which has an average titer of at least 32 for Dce cells in the slide test.

5. The method of claim 4 wherein the test slide is heated to about 40°–45° C. prior to mixing step (b).

6. An antibody reagent useful for rapidly determining the presence or absence of D antigen on red blood cells which comprises reduced, S-alkylated, anti-D IgG maintained at a pH of between about 7.5 and 8.3 by an effective buffering amount of a compatible buffer in a medium containing from about 6–10% by weight total protein, and which reagent has an average titer of at least 32 for Dce cells in the slide test or rapid tube test.

7. A method for preparing an antibody reagent useful for rapidly determining the presence or absence of D antigen on red blood cells, which antibody reagent has an average titer of at least 32 for Dce cells in the slide test or the rapid tube test, which comprises the steps of:

(a) obtaining a substantially lipid-free anti-D human antiserum;
   (b) adjusting the pH of said antiserum to about 8.6 by addition of an effective buffering amount of a compatible buffer;
   (c) reducing said buffered antiserum with a reducing agent;
   (d) S-alkylating said reduced buffered antiserum with an S-alkylating agent;
   (e) dialyzing said S-alkylated reduced antiserum at a pH between 7.5 and 8.3; and
   (f) adjusting the total protein concentration to about 6–10% by weight by addition of a nonspecific protein.

8. The method of claim 7 wherein the buffer used in step (b) is 2 M tris-(hydroxymethyl)aminomethane.

9. The method of claim 7 wherein the reducing step (c) is accomplished by mixing one volume of 0.04 M dithiothreitol in saline with about four volumes of the bufferend antiserum from step (b) and allowing the mixture to stand at about 20°–30° C. for at least about thirty minutes.

10. The method of claim 7 wherein the S-alkylating step (d) is accomplished by mixing one volume of 0.4 M iodoacetamide in distilled water with about four volumes of the reduced antiserum from step (c) and allowing the mixture to stand at about 20°–30° C. for at least about sixty minutes.

11. The method of claim 7 wherein the dialyzing step (e) is accomplished by twice dialyzing the S-alkylated antiserum from step (d) at about 2°–8° C. using about ten volumes of 0.15 M tris-(hydroxymethyl)aminomethane at a pH of about 7.5–8.3.

12. The method of claim 11 wherein the pH is about 7.7–8.1.

13. The product produced by the method of claim 7.

14. The product produced by the method of claim 8, 9, 10, or 11.

* * * * *